United States Patent
Broell et al.

(10) Patent No.: US 7,714,165 B2
(45) Date of Patent: May 11, 2010

(54) METHOD FOR THE CONTINUOUS PRODUCTION OF UNSATURATED CARBOXYLIC ACID ANHYDRIDES

(75) Inventors: Dirk Broell, Langen (DE); Hermann Siegert, Seeheim-Jugenheim (DE)

(73) Assignee: Evonik Roehm GmbH, Darmstadt (DE)

( * ) Notice: Subject to any disclaimer, the term of this patent is extended or adjusted under 35 U.S.C. 154(b) by 0 days.

(21) Appl. No.: 12/295,323

(22) PCT Filed: Mar. 14, 2007

(86) PCT No.: PCT/EP2007/052409

§ 371 (c)(1),
(2), (4) Date: Sep. 30, 2008

(87) PCT Pub. No.: WO2007/147653

PCT Pub. Date: Dec. 27, 2007

(65) Prior Publication Data

US 2009/0118533 A1 May 7, 2009

(30) Foreign Application Priority Data

Jun. 23, 2006 (DE) .................. 10 2006 029 318

(51) Int. Cl.
*C07C 51/54* (2006.01)
(52) U.S. Cl. ..................................... 562/892
(58) Field of Classification Search ............... None
See application file for complete search history.

(56) References Cited

U.S. PATENT DOCUMENTS

| | | | | |
|---|---|---|---|---|
| 2,178,752 A | * | 11/1939 | Gleason ................ | 562/892 |
| 4,857,239 A | * | 8/1989 | Hurtel et al. .......... | 562/896 |
| 6,743,407 B2 | | 6/2004 | Schaefer et al. | |
| 6,977,310 B2 | | 12/2005 | Ackermann et al. | |
| 6,979,432 B2 | | 12/2005 | Schaefer et al. | |
| 2006/0211880 A1 | | 9/2006 | Ackerman et al. | |
| 2008/0194862 A1 | | 8/2008 | Ackermann et al. | |
| 2008/0194875 A1 | | 8/2008 | Ackermann et al. | |
| 2008/0269431 A1 | | 10/2008 | Sarcinelli et al. | |

FOREIGN PATENT DOCUMENTS

EP  0 196 520  10/1986

OTHER PUBLICATIONS

U.S. Appl. No. 12/298,034, filed Oct. 22, 2008, May, et al.
U.S. Appl. No. 12/300,189, filed Nov. 10, 2008, Broell, et al.

(Continued)

*Primary Examiner*—Karl J Puttlitz
(74) *Attorney, Agent, or Firm*—Oblon, Spivak, McClelland, Maier & Neustadt, L.L.P.

(57) ABSTRACT

The invention relates to a method for the continuous production of unsaturated carboxylic acid anhydrides of general formula (I): R—C(O)—O—C(O)—R (I), wherein R is an unsaturated organic group with 2 to 12 C atoms, by reaction of a ketene with an unsaturated carboxylic acid of general formula (II): R—COOH (II), wherein R is defined as above, in an apparatus which has a reaction zone (1) for the reaction of a ketene with an unsaturated carboxylic acid of general formula (II), and a reaction zone (2) for the subsequent reaction of the crude anhydride mixture and a rectification column with an upper, a middle and a lower zone, in the sump of which an inert boiling oil is present.

18 Claims, 1 Drawing Sheet

OTHER PUBLICATIONS

Figure 1:
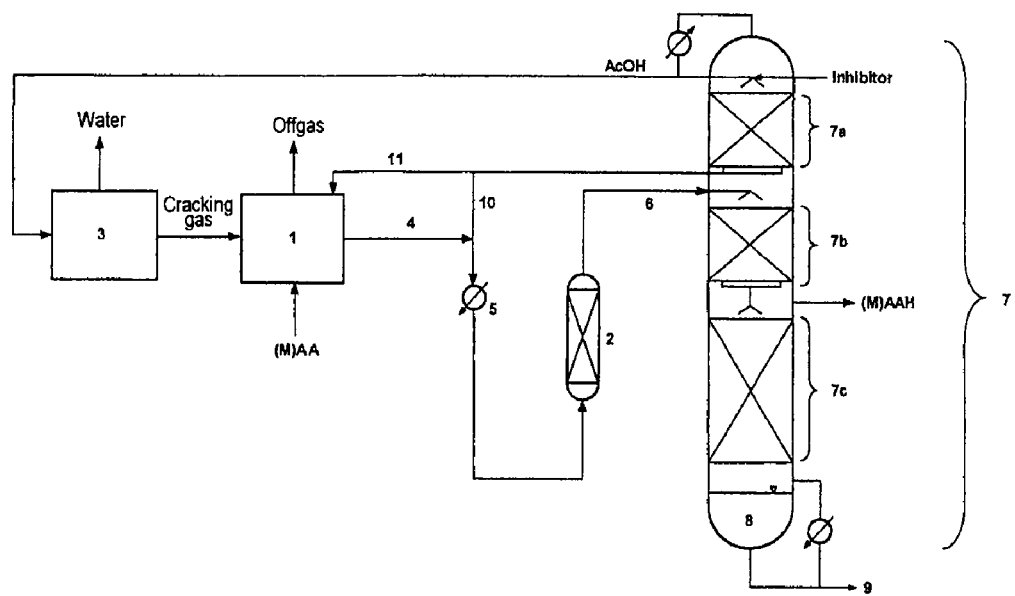

U.S. Appl. No. 12/299,217, filed Oct. 31, 2008, Broell, et al.
U.S. Appl. No. 12/307,773, filed Jan. 7, 2009, Ackermann, et al.
U.S. Appl. No. 12/441,145, filed Mar. 13, 2009, May, et al.
U.S. Appl. No. 12/515,036, filed May 15, 2009, May, et al.
U.S. Appl. No. 12/443,784, filed Mar. 31, 2009, Vogel, et al.
U.S. Appl. No. 12/442,415, filed Mar. 23, 2009, Vogel, et al.
U.S. Appl. No. 12/303,161, filed Dec. 2, 2008, Marx, et al.
U.S. Appl. No. 12/517,563, filed Jun. 4, 2009, Broell.

* cited by examiner

METHOD FOR THE CONTINUOUS PRODUCTION OF UNSATURATED CARBOXYLIC ACID ANHYDRIDES

The invention describes a process for the continuous preparation of unsaturated carboxylic anhydrides, in particular the reaction of an unsaturated carboxylic acid with a ketene.

DE-A-3510035 describes a process for the continuous preparation of unsaturated carboxylic anhydrides by means of an acid-catalysed transanhydridization reaction of acetic anhydride with an unsaturated carboxylic acid in the middle part of a distillation column. To achieve complete conversion, acetic anhydride is used in an excess of from 0.1 to 0.5 mol per mol of carboxylic acid, and a mixture of acetic acid and acetic anhydride is then obtained at the top of the column, i.e. pure acetic acid is not obtained.

Furthermore, the product formed is contaminated by the catalyst which has to be removed in a further process step.

U.S. Pat. No. 4,857,239 describes a process for preparing methacrylic anhydride, in which the molar ratio of methacrylic acid to acetic anhydride is from 2.1 to 3 and a polymerization inhibitor is introduced into the distillation column. According to the examples, the process is discontinuous. A further disadvantage is that the starting material used in excess is obtained unutilized.

US-A-2003/0018217 describes a batch process for preparing methacrylic anhydride, in which the initial molar ratio of methacrylic acid to acetic anhydride is preferably from 9 to 11. The acetic acid formed is immediately taken off and the reactor volume made free is filled up with acetic anhydride. To avoid polymerization, inhibitors are introduced into the reactor and into the column. Many by-products are formed and these cannot be removed completely.

It is therefore an object of the invention to provide an improved process for the continuous preparation of unsaturated carboxylic anhydrides, in which complete conversion of the unsaturated carboxylic acid used is achieved and at the same time the unsaturated carboxylic anhydride formed is obtained in high purity. Furthermore, polymerization should be largely avoided in all regions and the space-time yield of the reaction should be increased.

The invention provides a process for the continuous preparation of unsaturated carboxylic anhydrides of the general formula I

$$R-C(O)-O-C(O)-R \quad (I)$$

where R is an unsaturated organic radical having from 2 to 12 carbon atoms,
by reaction of a ketene with an unsaturated carboxylic acid of the general formula II

$$R-COOH \quad (II),$$

where R is as defined above,
characterized in that, in an apparatus containing
a reaction region (1) for the reaction of a ketene with an unsaturated carboxylic acid of the general formula II,
a reaction region (2) for the further reaction of the crude anhydride mixture formed and
a rectification column which has an upper, middle and lower region and whose bottom has been charged with an inert vaporization oil,
a) the unsaturated carboxylic acid of the general formula II is fed into the reaction region (1),
b) the crude anhydride mixture formed in step a) is fed into a further reaction region (2) which is located outside or within the column or is present in the reaction region (1),
c) the crude anhydride mixture from step b) is purified in the rectification column,
d) the carboxylic acid formed is taken off at the top of the column and is recirculated to ketene production,
e) the unreacted starting materials and intermediates formed are recirculated to the reaction region (1) and/or (2) and
f) the product of the formula I is obtained between the middle and lower regions of the rectification column.

As a result of these technical features, complete conversion of the starting materials and at the same time a high purity of the products are achieved and polymerization is largely avoided in all regions since, inter alia, long residence times of the unsaturated anhydride formed in the bottom of the column are ruled out.

Unsaturated carboxylic acids suitable for the process of the invention have an unsaturated organic radical having from 2 to 12, preferably from 2 to 6, particularly preferably from 2 to 4, carbon atoms.

Suitable alkenyl groups are the vinyl, allyl, 2-methyl-2-propenyl, 2-butenyl, 2-pentenyl, 2-decenyl, 1-undecenyl and 9,12-octadecadienyl groups. Particular preference is given to the vinyl and allyl groups.

Particularly preferred carboxylic acids include, inter alia, (meth)acrylic acids. The term (meth)acrylic acids is known to those skilled in the art and encompasses not only acrylic acid and methacrylic acid but also derivatives of these acids. These derivatives include, inter alia, β-methylacrylic acid (butenoic acid, crotonic acid), α,β-dimethylacrylic acid, β-ethylacrylic acid, α-chloroacrylic acid, α-cyanoacrylic acid, 1-(trifluoromethyl)acrylic acid and also β,β-di-methylacrylic acid. Preference is given to acrylic acid (propenoic acid) and methacrylic acid (2-methyl-propenoic acid).

Suitable ketenes for the process of the invention have the general formula III R'—CR"=C=O (III), where R' and R" are identical or different and are each hydrogen or a $C_1$-$C_4$-alkyl radical. Preference is given to using $CH_2$=C=O as ketene.

The preparation of ketene is carried out by customary methods known from the general technical literature, for example from H. Held, A. Rengstl and D. Mayer, Acetic Anhydride and Mixed Fatty Acid Anhydrides in Ullmann's Encyclopedia of Industrial Chemistry, 6th edition, Wiley VCH, Weinheim, 2003, pp. 184-185.

In the process of the invention, the ketene used as reactant is obtained by thermal dissociation of a carboxylic acid of the general formula IV R'—CR"H—COOH (IV), where R' and R" are as defined above, in a ketene furnace in the presence of a customary catalyst such as triethyl phosphate. Thermal dissociation is effected under generally customary temperature and pressure conditions.

Preference is given to the thermal dissociation of acetic acid, giving $CH_2$=C=O as ketene.

The apparatus suitable for the process of the invention has a reaction region or reactor (1) which is located outside the rectification column and is connected to the further components of the apparatus.

The ketene obtained is separated off by conventional methods and reacted with an unsaturated carboxylic acid of the general formula II R—COOH (II), where R is as defined above, in the reaction region (1). The crude anhydride mixture obtained reacts further in a reaction region or reactor (2). The reaction region (2) can be present outside and/or within the rectification column and/or in the reaction region (1).

The reaction region (2) is preferably located within or outside the rectification column, particularly preferably outside. At least one catalyst is preferably provided in this reaction region (2).

The molar ratio of the reactants, i.e. of unsaturated carboxylic acid of the formula II to ketene of the formula III, is usually from 1:4 to 8:1, preferably 2:1.

The reaction in the reaction region (2) is preferably carried out at temperatures in the range from 30 to 120° C., particularly preferably from 40 to 100° C., in particular from 50 to 80° C. The reaction temperature is dependent on the system pressure set. If the reaction region (2) is located within the column, the reaction is preferably carried out in the pressure range from 5 to 100 mbar (absolute), in particular from 10 to 50 mbar (absolute) and particularly preferably from 20 to 40 mbar (absolute).

If the reaction region (2) is located outside the column and is separate from the reaction region (1), other pressure and temperature conditions can be selected there. This has the advantage that the reaction parameters of the reactor (2) can be set independently of the operating conditions in the column and in the reaction region (1).

The reaction time depends on the reaction temperature; the residence time in the reaction region (2) on a single pass is preferably from 0.5 to 15 minutes, particularly preferably from 1 to 5 minutes.

In the preparation of (meth)acrylic anhydride from ketene $CH_2=C=O$ and (meth)acrylic acid, the reaction temperature in the reaction region (2) is preferably from 40 to 100° C., particularly preferably from 50 to 90° C., and very particularly preferably from 70 to 85° C.

The reaction mixture can comprise not only the reactants but also further constituents such as solvents, catalysts and polymerization inhibitors.

If a catalyst is used within the reaction region (2) within the rectification column, this catalyst can be provided in any region of the rectification column, preferably the middle region.

However, the catalyst is preferably provided in a reaction region (2) which is located outside the column and is separate from the reaction region (1). This arrangement of the catalyst region is preferred, with the crude anhydride mixture being continually passed through the catalyst region. As a result, the unsaturated carboxylic anhydride of the formula I, for example (meth)acrylic anhydride, and a carboxylic acid of the formula IV, for example acetic acid, which is recirculated to ketene production are formed continuously.

Preference is given to using heterogeneous catalysts in the reaction region (2). Particularly suitable heterogeneous catalysts are acidic fixed-bed catalysts, in particular acidic ion exchangers (cation exchangers).

Particularly useful acidic ion exchangers include, in particular, cation-exchange resins such as styrene-divinylbenzene polymers containing sulphonic acid groups. Suitable cation-exchange resins can be obtained commercially from Rohm&Haas under the trade name Amberlyst®, from Dow under the trade name Dowex® and from Lanxess under the trade name Lewatit®.

The amount of catalyst in 1 is preferably from 1/10 to 2 times, particularly preferably from 1/5 to 1/2, the amount of unsaturated carboxylic anhydride of the formula I to be produced in 1/h.

Polymerization inhibitors which can preferably be used include, inter alia, octadecyl 3-(3,5-di-tert-butyl-4-hydroxyphenyl) propionate, phenothiazine, hydroquinone, hydroquinone monomethyl ether, 4-hydroxy-2,2,6,6-tetra-methylpiperidinooxyl, (TEMPOL), 2,4-dimethyl-6-tert-butylphenol, 2,6-di-tert-butylphenol, 2,6-di-tert-butyl-4-methylphenol para-substituted phenylenediamines such as N,N'-diphenyl-p-phenylenediamine, 1,4-benzo-quinone, 2,6-di-tert-butyl-alpha-(dimethylamino)-p-cresol, 2,5-di-tert-butylhydroquinone or mixtures of two or more of these stabilizers. Very particular preference is given to phenothiazine.

The inhibitor can be introduced into the feed of the unsaturated carboxylic acid of the general formula II, upstream of the reaction region (1), upstream of the reaction region (2) and/or into the rectification column, preferably at the top of the column.

In the rectification column, the unsaturated carboxylic anhydride is preferably taken off as target product in gaseous form between the middle and lower regions. The recirculation of unreacted starting materials and intermediates formed to the reaction region is effected, for example, by means of a pump.

High boilers such as added inhibitors can be removed from the bottoms from the column by customary methods, for example by means of a thin film evaporator or an apparatus designed for similar tasks which recirculates vaporizing substances to the rectification column and discharges high boilers which do not evaporate.

As vaporization oil for the process of the invention, use is made of a high-boiling, inert substance which is thermally stable over a long time and has a boiling point higher than the boiling points of the components participating in the reaction in order to allow the acid anhydride formed to be separated off by distillation without polymerization. However, the boiling point of the vaporization oil should not be too high in order to reduce the thermal stress on the acid anhydride formed. The vaporization oil is located in the bottom of the column so as to avoid long residence times of the target product which is susceptible to polymerization.

In general, the boiling point of the vaporization oil at atmospheric pressure (1013 mbar) is from 200 to 400° C., in particular from 240 to 290° C.

Suitable vaporization oils are, inter alia, relatively long-chain unbranched paraffins having from 12 to 20 carbon atoms, aromatic compounds such as Diphyl (eutectic mixture of 75% of diphenyl oxide and 25% of biphenyl), alkyl-substituted phenols or naphthalene compounds, sulfolane (tetrahydrothiophene 1,1-dioxide) or mixtures of these.

Suitable examples are the vaporization oils shown below:

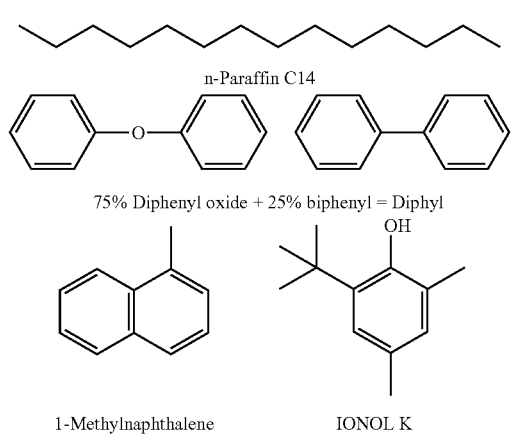

n-Paraffin C14

75% Diphenyl oxide + 25% biphenyl = Diphyl

1-Methylnaphthalene        IONOL K

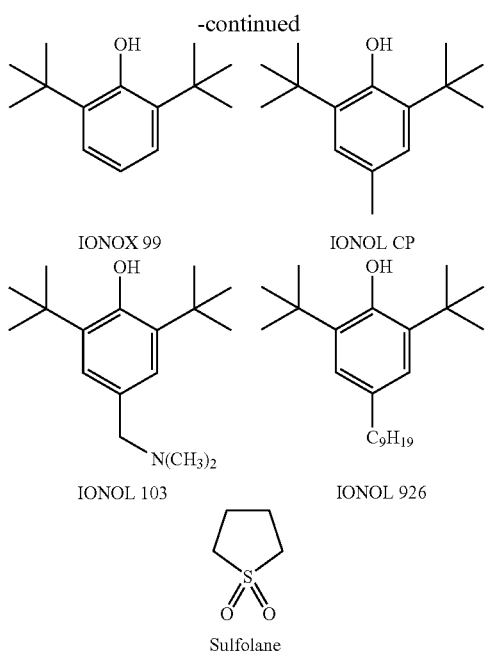

Particular preference is given to using 2,6-di-tert-butyl-para-cresol, 2,6-di-tert-butylphenol, sulfolane, Diphyl or mixtures of these, very particularly preferably sulfolane.

For the purification of the crude anhydride mixture obtained according to the present invention, it is possible to use any rectification column which has from 5 to 15 separation stages in each of the upper, middle and lower regions. The number of separation stages in the upper region is preferably from 10 to 15 and that in each of the middle and lower regions is preferably from 8 to 13. For the purposes of the present invention, the number of separation stages is the number of trays in a tray column multiplied by the tray efficiency or the number of theoretical plates in the case of a column containing ordered packing or a column containing random packing elements.

Examples of trays which may be present in a rectification column include ones such as bubble cap trays, sieve trays, tunnel trays, valve trays, slit trays, sieve slit trays, sieve bubble cap trays, nozzle trays, centrifugal trays; examples of random packing elements which may be present in a rectification column are ones such as Raschig rings, Lessing rings, Pall rings, Berl saddles, Intalox saddles and examples of ordered packing which may be present in a rectification column are those of the types Mellapak (Sulzer), Rombopak (Kühni), Montz-Pak (Montz) and ordered packing having catalyst pouches, for example Katapak (Sulzer).

A rectification column having combinations of regions of trays, regions of random packing elements and/or regions of ordered packing can likewise be used.

Preference is given to using a rectification column containing random packing elements and/or ordered packing.

The rectification column can be made of any material suitable for this purpose. Such materials include, inter alia, stainless steel and inert materials.

A preferred embodiment of the process of the invention is shown schematically in FIG. 1.

The preparation of ketene (3) is carried out by a customary method. A detailed description of ketene production may be found in, for example, H. Held, A. Rengstl and D. Mayer, Acetic Anhydride and Mixed Fatty Acid Anhydrides in Ullmann's Encyclopedia of Industrial Chemistry, 6th edition, Wiley VCH, Weinheim, 2003, pp. 184-185.

The subsequent reaction of ketene with (meth)acrylic acid (=(M)AA) is carried out in a reaction region (1), likewise by a customary method (see above H. Held et al., p. 185 ff.). The crude anhydride mixture (4) is then fed to a further reaction region (2). The temperature of the reactants can be adjusted by means of a heat exchanger (5) in the feed line.

The reactor (2) is preferably a flow tube reactor containing a fixed-bed catalyst. An acidic ion exchanger is preferably used as fixed-bed catalyst.

The stream (6) leaving the reactor is fed into the rectification column (7), preferably below the runback stream from the upper region (7a) of the column. The separation of the components takes place in the column (7). To avoid polymerization, inhibitor is preferably introduced at the top of the column and into the (M)AA feed.

In the upper region (7a), the low-boiling acetic acid is separated off from the intermediate boilers ((M)AA, intermediates), taken off at the top and recirculated to ketene production. In the middle region (7b) of the column, separation of intermediate boilers from (meth)acrylic anhydride (=(M)AAH) takes place, with (M)AAH preferably being taken off in gaseous form between the middle part and the lower part. In the lower region (7c) of the column, (M)AAH is separated from the vaporization oil (8) present in the bottom. High boilers present in the bottom can be removed by customary methods (9), for example by means of a thin film evaporator or an apparatus designed for similar tasks which recirculates vaporizing substances to the rectification column and discharges high boilers which do not vaporize.

The liquid stream resulting from the upper region (7a) is taken off in its entirety from the column and fed as recycle stream (10) together with the crude anhydride stream (4) to the reactor (2). As an alternative, the recycle stream (10) can also be fed in its entirety or in part to the reaction region (1) via line (11).

The invention claimed is:

1. A process for the preparation of unsaturated carboxylic anhydrides of the general formula I, comprising:

R—C(O)—O—C(O)—R    (I), preparing a ketene;
reacting the ketene with an unsaturated carboxylic acid of the general formula II

R—COOH    (II), in a first reaction region to produce a crude anhydride mixture;
further reacting the crude anhydride mixture in a second reaction region; and
separating the further reacted crude anhydride mixture in a rectification column to obtain a carboxylic acid fraction at a top of the rectification column, a fraction of purified unsaturated carboxylic anhydride of formula (I) between a middle and lower region of the rectification column and a fraction of unreacted starting materials and intermediate reaction materials formed in the first and second reaction regions in an upper portion of the rectification column;
wherein
the process for the preparation of unsaturated carboxylic anhydrides of the general formula I is continuous,
the rectification column has a top, upper, middle and lower region and a bottom,
the bottom of the rectification column is charged with an inert vaporization oil, the carboxylic acid fraction obtained at the top of the rectification column is recirculated to ketene production, the unreacted starting materials and intermediate reaction materials formed in the first and second reaction regions are recirculated to one or both of the first and second reaction regions, the purified unsaturated carboxylic anhydride of formula (I) is isolated, and R is an unsaturated organic radical having from 2 to 12 carbon atoms.

2. The process for the preparation of unsaturated carboxylic anhydrides of the general formula I, according to claim 1, wherein the second reaction region is located within the rectification column.

3. The process for the preparation of unsaturated carboxylic anhydrides of the general formula I, according to claim 1, wherein the second reaction region is located within the first reaction region.

4. The process for the preparation of unsaturated carboxylic anhydrides of the general formula I, according to claim 1, wherein a molar ratio of the unsaturated carboxylic acid of the general formula II to the ketene is from 1:4 to 8:1.

5. The process for the preparation of unsaturated carboxylic anhydrides of the general formula I, according to claim 1, further comprising adding a polymerization inhibitor to the rectification column.

6. The process for the preparation of unsaturated carboxylic anhydrides of the general formula I, according to claim 5, wherein the polymerization inhibitor is at least one selected from the group consisting of octadecyl 3-(3,5-di-tert-butyl-4-hydroxyphenyl)propionate, phenothiazine, hydroquinone, hydroquinone monomethyl ether, 4-hydroxy-2,2,6,6-tetramethylpiperidinooxyl (TEMPOL), 2,4-dimethyl-6-tert-butylphenol, 2,6-di-tert-butylphenol, 2,6-di-tert-butyl-4-methylphenol, para-substituted phenylenediamines such as N,N'-diphenyl-p-phenylenediamine, 1,4-benzoquinone, 2,6-di-tert-butyl-alpha-(dimethylamino)-p-cresol, 2,5-di-tert-butylhydroquinone or a mixture thereof.

7. The process for the preparation of unsaturated carboxylic anhydrides of the general formula I, according to claim 1, wherein the second reaction region is a flow tube reactor comprising a fixed bed catalyst.

8. The process for the preparation of unsaturated carboxylic anhydrides of the general formula I, according to claim 7, wherein the fixed bed catalyst is an acidic ion exchanger.

9. The process according to claim 1, wherein a heterogeneous catalyst is present in the second reaction region.

10. The process according to claim 9, wherein the heterogeneous catalyst is an acidic fixed-bed catalyst.

11. The process according to claim 9, wherein the heterogeneous catalyst is a cation exchanger.

12. The process according to claim 1, wherein the second reaction region is located outside the rectification column and is separate from the first reaction region.

13. The process according to claim 1, wherein
the unsaturated carboxylic anhydride of the formula I is (meth)acrylic anhydride the ketene is ketene of the formula CH2=C=O, and the unsaturated carboxylic acid of the general formula II is (meth)acrylic acid.

14. The process according to claim 1, wherein the inert vaporization oil charged to the bottom of the rectification column is a high-boiling, inert substance having a boiling point higher than the boiling points of the components participating in the reaction.

15. The process according claim 14, wherein the inert vaporization oil is at least one selected from the group consisting of 2,6 di-tert-butyl-para-cresol, 2,6 di-tert-butylphenol, sulfolane, Diphyl and a mixture thereof.

16. The process according to claim 15, wherein the inert vaporization oil is sulfolane.

17. The process according to claim 1, further comprising removing high-boiling components from the bottom of the column, separating vaporizing substances contained in the inert vaporizing oil from high boiling materials which do not vaporize and recirculating the vaporizing substances to the column.

18. The process for the preparation of unsaturated carboxylic anhydrides of the general formula I, according to claim 17, wherein the separating vaporizing substances comprising the inert vaporizing oil from high boiling materials which do not vaporize comprises a thin film evaporator or apparatus designed for a similar task.

\* \* \* \* \*